United States Patent
Rose

(10) Patent No.: US 11,905,310 B2
(45) Date of Patent: Feb. 20, 2024

(54) PROTEIN PURIFICATION

(71) Applicant: UCB BIOPHARMA SRL, Brussels (BE)

(72) Inventor: Michael Harry Rose, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 218 days.

(21) Appl. No.: 17/327,865

(22) Filed: May 24, 2021

(65) Prior Publication Data

US 2021/0323999 A1    Oct. 21, 2021

Related U.S. Application Data

(63) Continuation of application No. 15/999,655, filed as application No. PCT/EP2017/053677 on Feb. 17, 2017, now abandoned.

(30) Foreign Application Priority Data

Feb. 19, 2016   (GB) .................................... 1602938

(51) Int. Cl.
 *C07K 1/18*    (2006.01)
 *C07K 1/22*    (2006.01)
 *C07K 1/16*    (2006.01)

(52) U.S. Cl.
 CPC ................ *C07K 1/18* (2013.01); *C07K 1/16* (2013.01); *C07K 1/165* (2013.01); *C07K 1/22* (2013.01)

(58) Field of Classification Search
 CPC . C07K 1/16; C07K 1/165; C07K 1/18; C07K 1/22; B01D 15/361; B01D 15/362; B01D 15/363; B01D 15/364; B01D 15/14; B01D 15/1814
 See application file for complete search history.

(56) References Cited

U.S. PATENT DOCUMENTS

| | | | |
|---|---|---|---|
| 4,267,054 A | 5/1981 | Yoritomi et al. | |
| 2009/0050566 A1* | 2/2009 | Kozlov | B01J 20/28033 427/551 |
| 2009/0149638 A1 | 6/2009 | Ley et al. | |
| 2013/0213884 A1* | 8/2013 | Lacki | B01D 15/1871 210/85 |

FOREIGN PATENT DOCUMENTS

| | | |
|---|---|---|
| CN | 101318991 | 12/2008 |
| WO | WO 2012/013682 | 2/2012 |
| WO | WO 2013/068571 | 5/2013 |
| WO | WO 2014/158231 | 10/2014 |
| WO | WO-2014158231 A1 * | 10/2014 ............. C07K 1/165 |

OTHER PUBLICATIONS

Poros Anion Exchange Resins: XQ, HQ 50, PI 50 and D 50, Product Information Sheet, *Applied Biosystems Life Technologies*, Mar. 3, 2015, Pub. No. 100031320, Rev. A, pp. 1-8.
"Affinity purification of antibodies" 2006, available online at https://web.archive.org/web/20100705010853/http://tryps.rockefeller.edu/Protocols/antibody_affinity_ns.pdf, pp. 1-2.
"Affinity purification of antibiodies [sic] using His-tagged Protein" 2015, available online at https://langdalelab.files.wordpress.com/2015/07/affinity_purif_ab.pdf, pp. 1-2.
"Antigen-Affinity Purification of Antibodies" 2012, available online at http://www.abbiotec.com/sites/default/files/lp113-antigen-affinity_antibody_purification.pdf, pp. 1-3.
Clackson, T. et al. "Making antibody fragments using phage display libraries" *Nature*, Aug. 15, 1991, pp. 624-628, No. 352.
Crommelin, D. J. A. et al. (eds.) *Pharmaceutical Biotechnology, 3rd Edition*, 2008, pp. 58-62.
Dunn, S. D. "Removal of the $\epsilon$ subunit from *Escherichia coli* $F_1$-ATPase Using Monoclonal Anti-$\epsilon$ Antibody Affinity Chromatography" *Analytical Biochemistry*, 1986, pp. 35-42, vol. 159.
Kontermann, R. E. "Dual targeting strategies with bispecific antibodies" *MAbs*, 2012, pp. 182-197, vol. 4, Issue 2.
Mahajan, E. et al. "Improving affinity chromatography resin efficiency using semi-continuous chromatography" *Journal of Chromatography A*, 2012, pp. 154-162, vol. 1227.
Written Opinion in International Application No. PCT/EP2017/053677, dated May 15, 2017, pp. 1-5.
GB Search Report in Application No. GB1602938.1, dated Nov. 16, 2016, pp. 1-6.
Read, A.J. et al. "Purification of polyclonal anti-conformational antibodies for use in affinity selection from random peptide phage display libraries: A study using the hydatid vaccine EG95" *Journal of Chromatography B Analytical Technologies in the Biomedical and Life Sciences*, 2009, pp. 1-16, vol. 877, No. 14-15.
Rahmatullah, M. et al. "Direct Interaction of the $\alpha$ and $\gamma$ Subunits of the G Proteins" *The Journal of Biological Chemistry*, Feb. 4, 1994, pp. 3574-3580, vol. 269, No. 5.

* cited by examiner

*Primary Examiner* — Ryan B Huang
(74) *Attorney, Agent, or Firm* — SALIWANCHIK, LLOYD & EISENSCHENK

(57) ABSTRACT

The present invention relates to a process for purification a protein comprising a semi-continuous chromatography step whereby the flow-through is collected and re-loaded onto the chromatography matrix.

16 Claims, 13 Drawing Sheets

Figure 8

| | Cycle 1 | Cycles 2-4 | Cycle 5 |
|---|---|---|---|
| Stripping (CVs) | 2 | 2 | 2 |
| Cleaning (CVs) | 2 | 2 | 2 |
| CIP hold (minutes) | 15 | 15 | 15 |
| Equilibration (CVs) | 3 | 3 | 3 |
| Recycle (CVs) | 0 | 9.45 | 9.45 |
| Fresh Load (CVs) | 15.44 | 11.27 | 7.89 |
| Fresh Load and recycle collection (CVs) | 8.12 | 8.12 | 0 |
| Wash and recycle collection (CVs) | 1.33 | 1.33 | 0 |
| Washing (CVs) | 1.67 | 1.67 | 3 |
| Elution (CVs) | 5 | 5 | 5 |
| total time (minutes) | 66.42 | 73.45 | 58.12 |

Figure 12

| | Traditional operation | Startup cycle | Running cycle 1 | Running cycle 2 | Running cycle 3 | Final cycle | new running cycle average | new overall | new overall improvement |
|---|---|---|---|---|---|---|---|---|---|
| load mg/ml (matrix) | 20.03 | 39.11 | 32.19 | 32.19 | 32.19 | 7.89 | 32.19 | 28.71 | 43.30% |
| eluate conc. mg/ml | 6.98 | 9.63 | 9.72 | 9.75 | 9.71 | 7.58 | 9.73 | 9.28 | 32.92% |
| eluate vol. ml | 26.16 | 30.43 | 30.23 | 29.80 | 30.08 | 25.41 | 30.04 | 29.19 | 11.58% |
| eluate quantity mg | 182.60 | 293.04 | 293.84 | 290.55 | 292.08 | 192.61 | 292.16 | 270.82 | 48.32% |
| yield % | 97.86% | 80.46%* | 98.02% | 96.93% | 97.44% | 262.12%* | 97.46% | 101.28% | 3.82% |
| impurities % | 11.54% | 7.66% | 7.98% | 7.79% | 7.77% | 12.19% | 7.85% | 8.66% | 33.26% |
| productivity mg/ml/hour | 23.52 | 28.37 | 25.65 | 25.65 | 25.65 | 20.68 | 25.65 | 25.34 | 7.74% |

Figure 13

| | Traditional operation | Startup cycle | Running cycle 1 | Running cycle 2 | Running cycle 3 | Final cycle | new running cycle average | new overall | new overall improvement |
|---|---|---|---|---|---|---|---|---|---|
| load mg/ml (matrix) | 29.68 | 63.21 | 56.98 | 56.98 | 56.98 | 30.96 | 56.98 | 53.03 | 78.66% |
| eluate conc. mg/ml | ? | 14.20 | 14.30 | 14.30 | 14.20 | 11.90 | 14.27 | 13.78 | ? |
| eluate vol. ml | ? | 34.76 | 36.60 | 36.41 | 36.52 | 33.26 | 36.51 | 35.51 | ? |
| eluate quantity mg | ? | 493.59 | 523.38 | 520.66 | 518.58 | 395.79 | 520.88 | 489.33 | ? |
| yield % | >98% | 83.84%* | 98.62% | 98.11% | 97.72% | 137.26%* | 98.15% | 99.09% | ~1% |
| productivity mg/ml/hour | 15.25 | 35.72 | 28.90 | 28.90 | 28.90 | 17.47 | 25.65 | 17.42 | 14.25% |

Figure 14

| | Traditional operation | Startup cycle | Running cycle 1 | Running cycle 2 | Running cycle 3 | Final cycle | new running cycle average | new overall | new overall change |
|---|---|---|---|---|---|---|---|---|---|
| load mg/ml (matrix) | 47.9 | 84.1 | 68.5 | 68.5 | 68.5 | 22.9 | 68.5 | 62.5 | 30.5% |
| eluate conc. mg/ml | 21.0 | 32.9 | 31.9 | 31.3 | 31.4 | 17.2 | 31.2 | 28.8 | 37.8% |
| eluate vol. CVs | 2.2 | 2.1 | 2.1 | 2.1 | 2.1 | 1.9 | 2.1 | 2.1 | 93.6% |
| eluate quantity mg | 8780 | 12900 | 12600 | 12400 | 12400 | 6200 | 12500 | 11300 | 28.7% |
| yield % | 96.2 | 80.7* | 96.5 | 95.2 | 95.3 | 142.4* | 95.7 | 94.9 | -1.3% |
| productivity mg/ml/hour | 20.9 | 16.3 | 21.1 | 20.9 | 20.9 | 41.6 | 21.0 | 19.7 | -5.7% |

PROTEIN PURIFICATION

CROSS-REFERENCE TO RELATED APPLICATIONS

This application is a continuation of U.S. application Ser. No. 15/999,655, filed Aug. 20, 2018, which is the U.S. national stage application of International Patent Application No. PCT/EP2017/053677, filed Feb. 17, 2017.

FIELD OF THE INVENTION

The present invention is in the field of protein purification. More specifically, it relates to a process for the purification of a protein of interest, such as an antibody or an antibody fragment using a semi-continuous chromatography step.

BACKGROUND OF THE INVENTION

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors. The protein of interest must be isolated from the mixture of compounds fed to the cells and from the by-products of the cells themselves (feed stream) to purity sufficient for use as a human therapeutic. The standards set by health authorities for proteins intended for human administration regarding impurities from the feed stream are very high. Many purification methods for proteins known in the art contain steps requiring the application e.g. of low or high pH, high salt concentration or other extreme conditions that may irreversibly jeopardize the biological activity of the protein to be purified and are therefore not suitable. Thus, separation of the desired protein to sufficient purity poses a formidable challenge. Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Antibodies and antibody fragments are of increasing importance in a range of therapeutic areas. One of the most important methods of producing antibodies and antibody fragments is by recombinant technology. Such techniques use a host cell to express the desired antibody, or a, which is then separated from the production medium and purified.

Antibodies require glycosylation and are therefore generally expressed in eukaryotic expression systems employing eukaryotic cells, in particular mammalian cells such as CHO, PER.C6, NS0, BHK or Sp2/0 cells. In eukaryotic expression systems the protein of interest expressed such as an antibody is generally secreted into the cell culture medium. The medium can subsequently be separated easily from the protein secreting cells, e.g. by centrifugation or filtration.

Almost all current industrial antibody purification platforms use Protein A. Protein A is a cell surface protein found in the cell wall of the bacteria *Staphylococcus aureus* that binds to the Fc portion of mammalian immunoglobulin. Protein A has a high affinity to human $IgG_1$ and $IgG_2$ and a moderate affinity to human IgM, IgA and IgE antibodies. Consequently, protein A purification is not well suited for antibody fragments that lack the Fc portion.

Affinity chromatography separates proteins on the basis of a reversible interaction between a protein (or group of proteins) of interest and a specific ligand coupled to a chromatography matrix. The interaction between the protein of interest and ligand coupled to the chromatography matrix can be a result of electrostatic or hydrophobic interactions, van der Waals' forces and/or hydrogen bonding. To elute the target molecule from the affinity medium the interaction can be reversed, either specifically using a competitive ligand, or non-specifically, by changing the pH, ionic strength or polarity. Affinity purification requires a ligand that can be covalently attached to a chromatography matrix. The coupled ligand must retain its specific binding affinity for the target molecules and, after washing away unbound material, the binding between the ligand and target molecule must be reversible to allow the target molecules to be removed in an active form. Despite its common use, affinity chromatography is costly, particularly at the industrial scale necessary to purify therapeutic proteins.

Ion exchange chromatography can be used to purify ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. Elution of molecules that are bound to the solid phase is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). Two general types of interaction are known: Anionic exchange chromatography mediated by negatively charged amino acid side chains (e.g. aspartic acid and glutamic acid) interacting with positively charged surfaces and cationic exchange chromatography mediated by positively charged amino acid residues (e.g. lysine and arginine) interacting with negatively charged surfaces. Anion exchangers can be classified as either weak or strong. The charge group on a weak anion exchanger is a weak base, which becomes de-protonated and, therefore, loses its charge at high pH. Diethylaminoethyl (DEAE)-cellulose is an example of a weak anion exchanger, where the amino group can be positively charged below pH-9 and gradually loses its charge at higher pH values. DEAE or diethyl-(2-hydroxy-propyl)aminoethyl (QAE) have chloride as counter ion, for instance.

An alternative to elution by increase in ion strength of the elution buffer (elution chromatography) is elution using molecules which have a higher dynamic affinity for the stationary phase than the bound protein. This mode of performing ion-exchange chromatography is called displacement chromatography. Displacement chromatography is fundamentally different from any other modes of chromatography in that the solutes are not desorbed in the mobile phase modifier and separated by differences in migration rates. In displacement, molecules are forced to migrate down the chromatographic column by an advancing shock wave of a displacer molecule that has a higher affinity for the stationary phase than any component from the feed stream. It is this forced migration that results in higher product concentrations and purities compared to other modes of operation, of high retention, followed by a constant infusion of a displacer solution into the column.

Chromatography matrices used for the various chromatography techniques, particularly for large, industrial scale purification processes, are very expensive. They are generally reused following cleaning. Due to the harsh nature of the cleaning agents used, chromatography matrix efficiency decreases over time. Typically, chromatography matrices are not used very efficiently in the art as their full maximum protein binding capacity is not exploited. In the art chromatography matrices are used such that they are loaded with protein of interest below their full capacity to improve yields. When protein matrices are loaded with protein of interest to their full capacity a lot of protein of interest is lost in the flow-through. Due to the high costs and the limited lifetime of chromatography matrices there is a need in the art for processes which optimally use a chromatography matrix.

Crude protein preparations from large scale cell culture processes typically cannot be purified in a single purification cycle. Due to the amount of protein to be purified several cycles of the same purification process are required to purify the output of the cell culture. The protein mixture to be purified is therefore frequently purified batch by batch in multiple purification cycles involving also multiple chromatography cycles. Continuous processes have also been implemented in large scale manufacturing processes for biopharmaceuticals. In continuous chromatography, several identical columns are connected in an arrangement that allows columns to be operated in series and/or in parallel, depending on the method requirements. Compared to single column or batch chromatography, wherein a single chromatography cycle is based on several consecutive steps, such as loading, wash, elution and regeneration, in continuous chromatography based on multiple identical columns all these steps occur simultaneously but on different columns each. Continuous chromatography operation results in a better utilization of chromatography resin, reduced processing time and reduced buffer requirements, all of which benefits process economy. A specific way of operating continuous chromatography is called simulated moving bed (SMB) chromatography. In simulated moving bed chromatography all the chromatography columns comprising the system are periodically and simultaneously moved in the direction opposite to the sample flow. The movement of the columns is realized by appropriate redirections of inlet and outlet stream to/from the columns which requires a sophisticated setup.

A semi-continuous chromatography process has been described in the art whereby rather than a single large chromatography column multiple smaller columns were used in row and loaded to a higher binding capacity. The flow-through of each column was directly loaded onto the following column. Alternatively, the flow-through of the first column was directed back to the first container harboring a mixture with protein of interest and then re-loaded onto the first column (Mahajan, George et al. 2012).

Using several chromatography columns in row requires sophisticated flow control apparatus and control software, as well as additional chromatography hardware including pumps, valves, detectors and housing for each additional column, which add cost, increase the probability of part failure, increase the complexity of validation processes and complicate diagnosis of errors. Furthermore, in order to align the flow-through from one column to the correct period in the sequence for the adjoined receiving column, delay periods must be introduced such that they match, which reduces the operational speed. Since each additional receiving column must be started and stopped in staggered sequence resulting in columns that are inactive during these periods, an additional productivity penalty is incurred each time the operation is shut down or restarted.

There is therefore still a need in the art for simple, efficient and costs effective processes for purification of proteins involving the use of chromatography matrices.

SUMMARY OF THE INVENTION

The present invention addresses the above-identified need by providing a novel process for the purification of a protein of interest which involves more efficient and cost effective use of chromatography matrices while maintaining or improving yield and purity of the purified protein.

Therefore, in a first aspect, the invention provides a process for the purification of a protein of interest from a mixture comprising the steps of
a) in an operational chromatography cycle loading a first volume of a mixture containing the protein of interest from a first container to a chromatography matrix operated such that the protein binds to the chromatography matrix until 40 to 100%, 50 to 100%, 60 to 100%, 70 to 100%, 80 to 100%, 90 to 100%, 70 to 90% or 70 to 80%%, 60 to 90%, 60 to 80% of the maximum static binding capacity of the chromatography matrix is reached;
b) collecting flow-through containing unbound protein of interest in a second container, and
c) in a further operational chromatography cycle re-loading the flow-through from the second container and loading a second volume of the protein of interest from the first container to the same chromatography matrix operated such that the protein of interest binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached.

In a second aspect the invention provides a process for the purification of a protein of interest from a mixture comprising the steps of:
a) in an operational chromatography cycle loading a first volume of a mixture containing the protein of interest from a first container to a chromatography matrix operated such that the dynamic binding capacity of the chromatography matrix is exceeded;
b) collecting flow-through containing unbound protein of interest in a second container, and
c) in a further operational chromatography cycle re-loading the flow-through from the second container and loading a second volume of the protein of interest from the first container to the same chromatography matrix, operated such that the dynamic binding capacity of the chromatography matrix is exceeded.

In a further embodiment the invention provides a process according to the second aspect, wherein in step (a) the loading of the protein of interest is stopped when at least 40% 50%, 60%, 70%, 80%, 90% or 100% of the maximum static binding capacity is reached.

In a further embodiment of the first or second aspect the invention provides a process, wherein the collection of the flow-through is started at a predetermined first concentration of protein of interest in the flow-through and stopped at a predetermined second concentration of protein of interest in the flow-through.

In a further embodiment of the first or second aspect the invention provides a process, wherein the chromatography is selected from affinity chromatography, such as Protein A chromatography, anion or cation exchange chromatography, hydrophobic interaction chromatography, mixed-mode chromatography, such as hydroxyapatite chromatography, chiral chromatography or dielectric chromatography.

In a further embodiment of the first or second aspect the invention provides a process, wherein one, two, three or all of the chromatography matrix/matrices for one, two, three, four or all chromatography steps is/are a chromatography column(s).

In a further embodiment of the first or second aspect the invention provides a process, wherein the protein of interest is an antibody or an antibody fragment.

In a further embodiment of the first or second aspect the invention provides a method of manufacture of a protein of interest comprising the process for purification according to embodiments of the invention.

In a further embodiment of the first or second aspect the invention provides a protein obtained by the method of manufacture of a protein of interest comprising the process for purification according to embodiments of the invention.

BRIEF DESCRIPTION OF THE FIGURES

FIG. 3 shows the distribution of concentration of protein of interest (target compound) when overloading the chromatographic matrix in a controlled way. The chromatographic matrix may be loaded with load material containing target compound until such time that a significant portion passes through the matrix without binding while some additional quantity of the target compounds continues to be bound. The extent of this overloading need not be to the point of saturation. This overloading material containing unbound target compound may be directed to the recycle container, and the zone that is collected need not include the entire length and may start after the target compound begins to leak through and end before the emerging target compound stops leaking through.

FIG. 8 shows a table of operational block settings in column volumes for each of the three cycle types (initial cycle, running cycle and final cycle) operating in the proposed methodology.

FIG. 12 shows a table of summarised results for operating the process according to the invention of a Fab at 900 cm/h on a 20 cm Capto S column. Yields are calculated on the basis of eluate released vs product loaded for that cycle. Since the startup cycle is additionally overloaded producing the recycle for the next cycle its yield is artificially depressed, and since the final cycle is relatively underloaded to prevent an excess recycle its yield is artificially high as it receives recycle from the previous cycle in addition to the fresh load applied which all elutes off together, giving an apparent yield of greater than 100%. The overall yield of the process is marginally greater than 100% which is within the tolerance of measurements and indicates essentially complete recovery of the loaded protein.

FIG. 13 shows a table of summarised results for operating the process according to the invention of a MAb at 500 cm/h on a 20 cm MabSelect SuRE LX column. Yields are calculated on the basis of eluate released vs product loaded. Since the startup cycle is additionally overloaded producing the recycle for the next cycle its yield is artificially depressed, and since the final cycle is relatively underloaded to prevent an excess recycle its yield is artificially high as it receives recycle from the previous cycle in addition to the fresh load applied which all elutes off together, giving an apparent yield of greater than 100%. The overall improvement gives an accurate measure of total output vs total input.

FIG. 14 shows a table of summarised results for operating the process according to the invention of a MAb at 150 cm/h on a 10 cm MabSelect SuRE LX column. Yields are calculated on the basis of eluate released vs product loaded. Since the startup cycle is additionally overloaded producing the recycle for the next cycle its yield is artificially depressed, and since the final cycle is relatively underloaded to prevent an excess recycle its yield is artificially high as it receives recycle from the previous cycle in addition to the fresh load applied which all elutes off together, giving an apparent yield of greater than 100%. The overall improvement gives an accurate measure of total output vs total input.

DETAILED DESCRIPTION OF THE INVENTION

Figure 1:
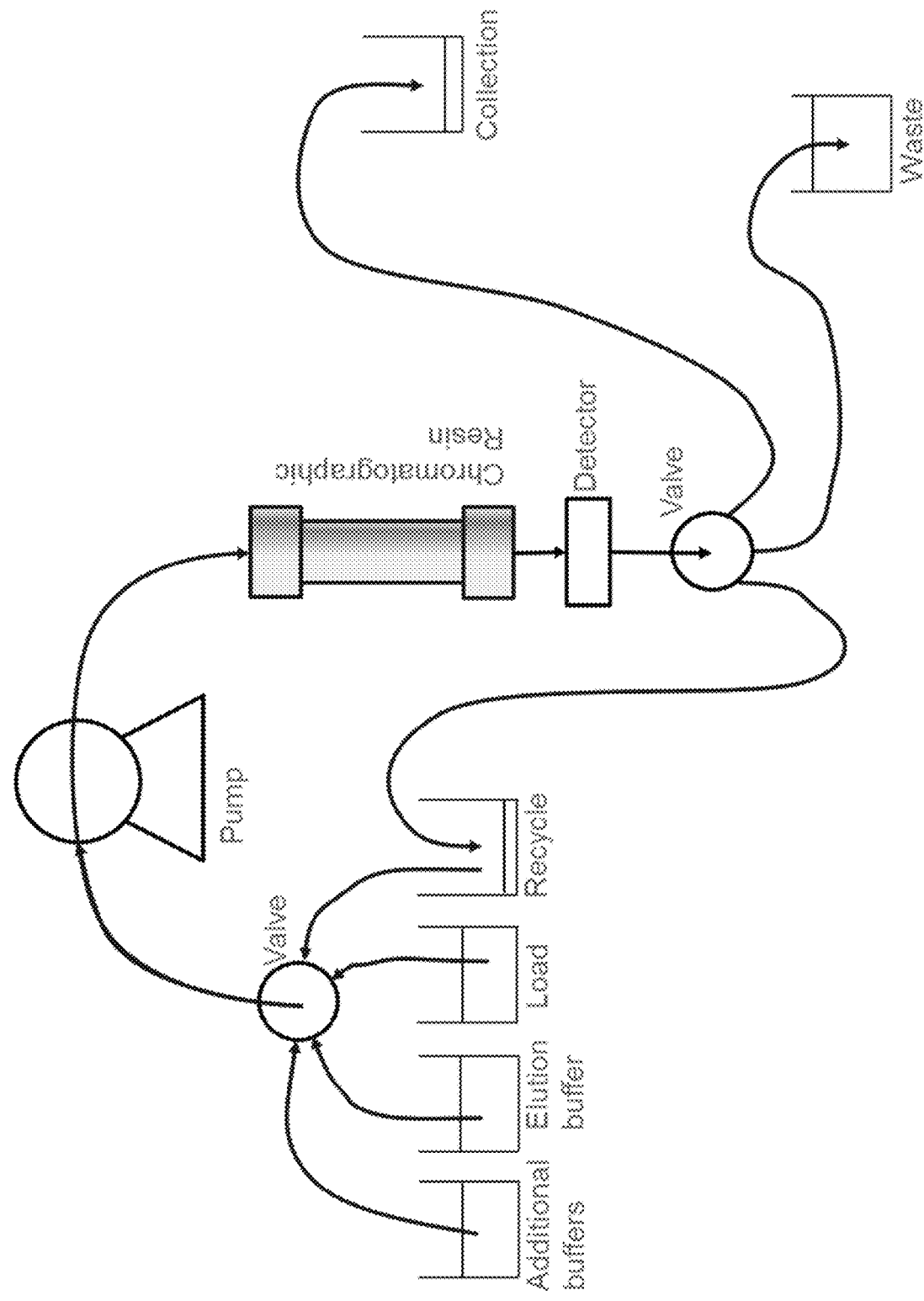
FIG. 1 shows a schematic diagram of the setup of the semi-continuous process. Various liquid buffer components are held in tanks and are sequentially pumped via a valve through a porous chromatographic matrix. After emerging from the matrix the flow-through passes through a detector which analyses the flow-through. The flow-through is then directed either for collection if it contains protein of interest in relevant amount or to waste. In the instant invention the flow-through may alternatively be directed to a separate recycle tank. The contents of this tank may then be pumped sequentially back onto the chromatographic matrix together with fresh load in one of the following operational chromatography cycles.
Figure 2:
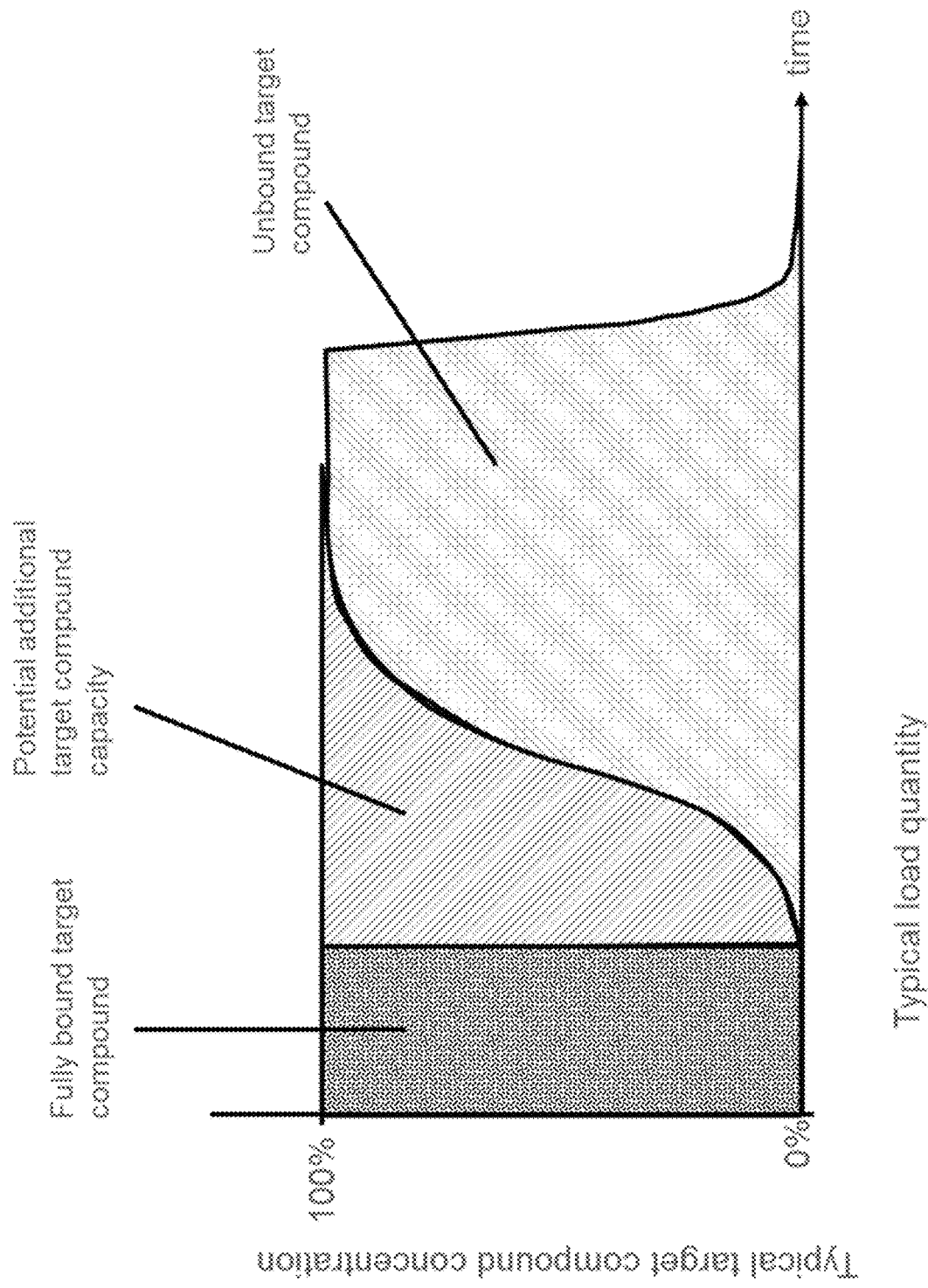
FIG. 2 shows the distribution of concentration of protein of interest (target compound) when overloading the chromatography matrix. When loading an immobilised chromatography matrix under dynamic conditions such as through continuous flowing of load material, the desired target compound in the stream is initially fully bound by the matrix. However, as the capacity of the matrix for the target compound progressively fills up, some of the target compound is bound and some leaks off and flows through alongside the other unwanted proteins in the load stream (e.g. host cell protein or protein by-products) and comes off in the flow-through. After some time the matrix becomes fully saturated with the target compound and cannot bind anymore and all the target compound, and any additional load material remains unbound and passes through the matrix.
Figure 3:
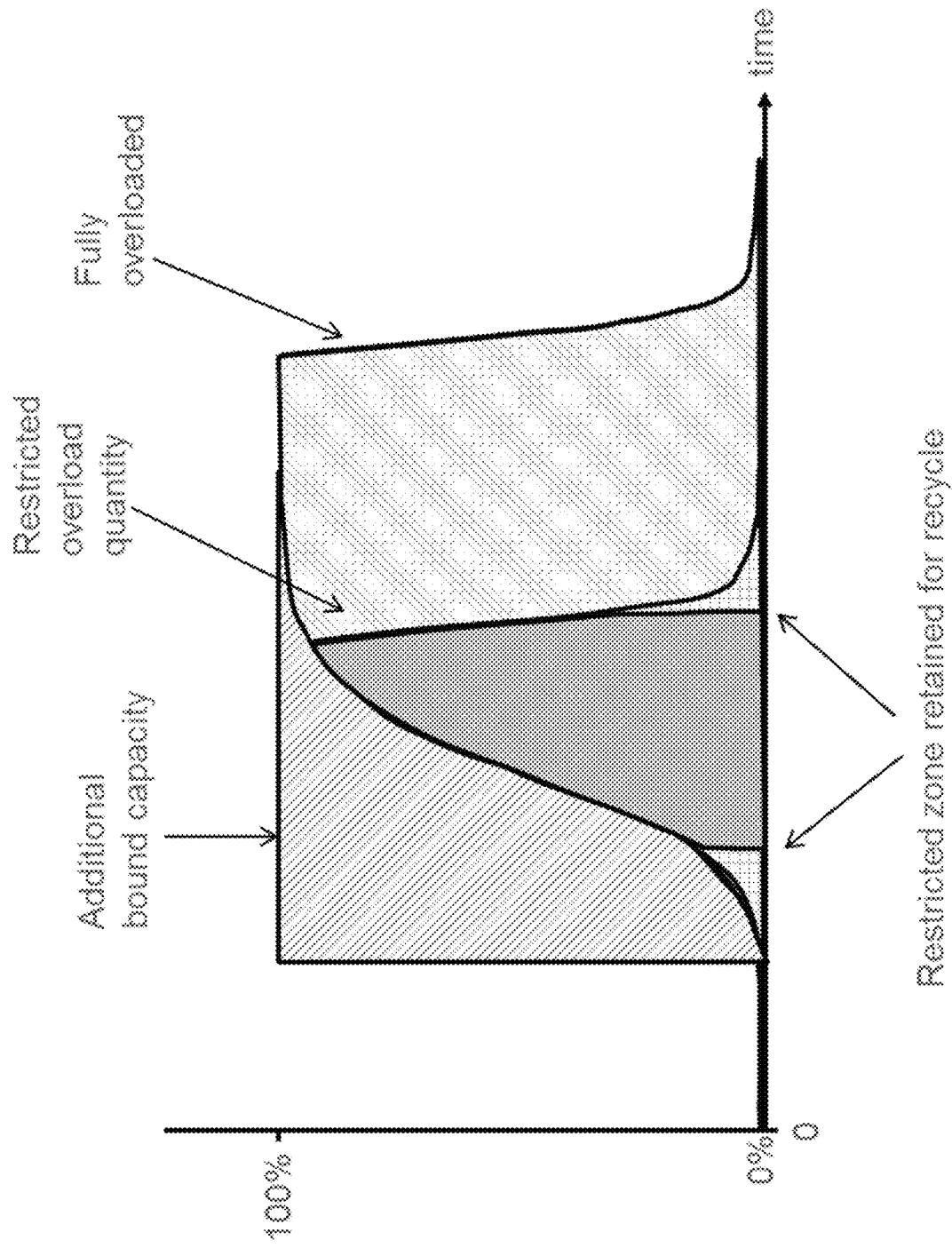
Figure 4:
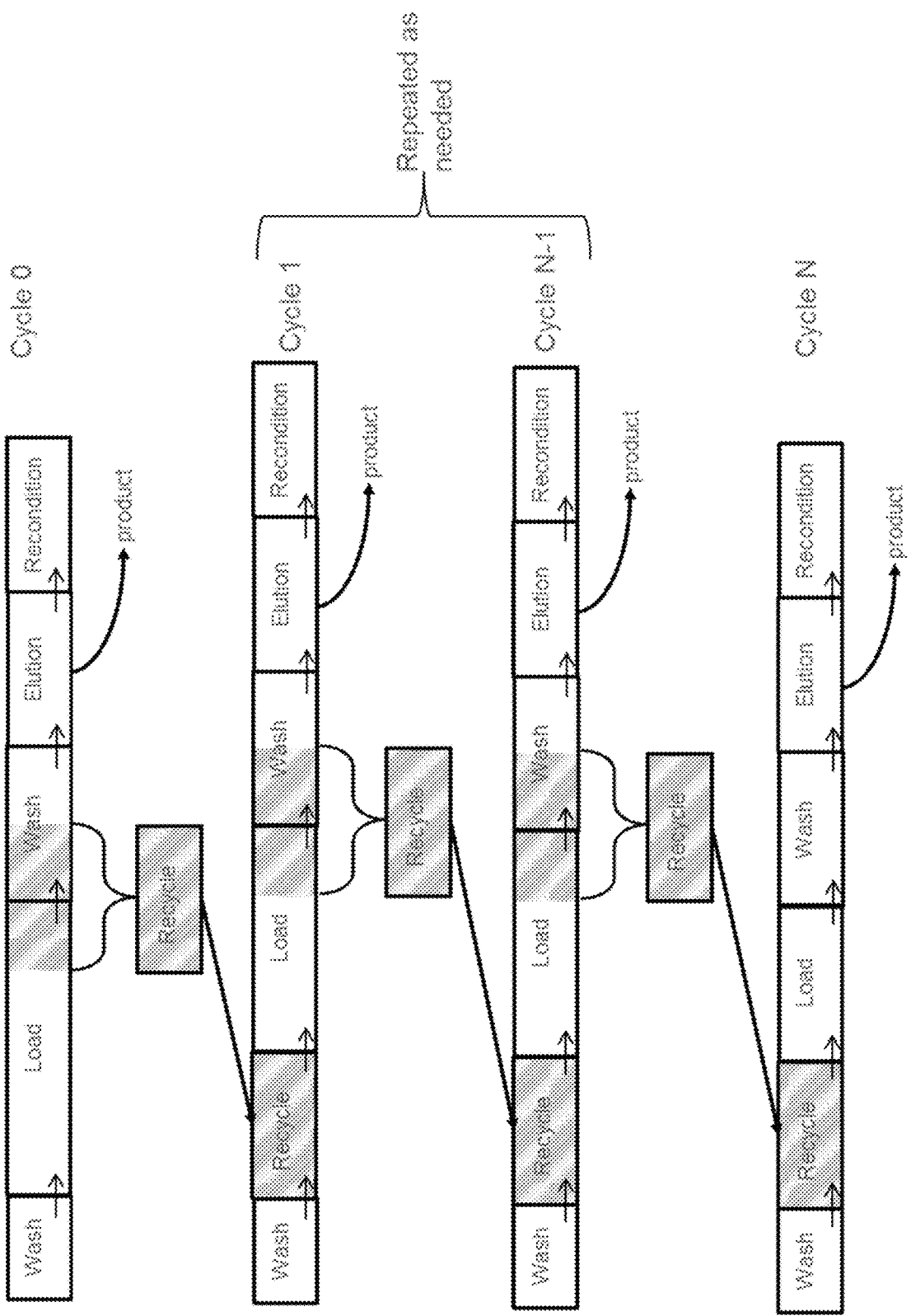
FIG. 4 shows a diagram of the process according to the invention. A typical chromatographic separation may involve a binding stage where protein of interest (target compound) binds to the immobilised matrix, and an elution stage where the target compound is chemically removed from the matrix. In between there are typically wash and conditioning steps to remove further impurities and maintain the quality of the matrix, during which these materials are typically directed to waste. In the new process according to the instant invention load containing the target compound is applied until it leaks through. A portion of this is retained in a recycle container. In a subsequent cycle in the process of the invention this is reapplied to the matrix before additional loading material containing target compound is applied. Again, this is applied until the matrix is overloaded and target compound leaks through. It is then directed to the recycle container. This process is repeated for as many cycles as desired, then in a final cycle a smaller amount of fresh load is applied and no recycle is collected.

A new process for the purification of a protein of interest has now been developed by the inventors of the instant invention which involves more efficient and cost effective use of chromatography matrices while maintaining or improving yield and purity of the purified protein.

In a first aspect the invention provides a process for the purification of a protein of interest from a mixture comprising the steps of
 a) in an operational chromatography cycle loading a mixture containing the protein of interest from a first container to a chromatography matrix operated such that the protein binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached;
 b) collecting flow-through containing unbound protein of interest in a second container, and
 c) in a further operational chromatography cycle re-loading the flow-through from the second container to the same chromatography matrix operated such that the protein of interest binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached.

In a variation of the first aspect the invention provides a process for the purification of a protein of interest from a mixture comprising the steps of
 d) in an operational chromatography cycle loading a mixture containing the protein of interest from a first container to a chromatography matrix operated such that the protein binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached;
 e) collecting flow-through containing unbound protein of interest in a second container, and
 f) re-loading the flow-through from the second container to the same chromatography matrix and additionally loading fresh load mixture in a further operational chromatography cycle operated such that the protein of interest binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached.

In another variation of the first aspect the invention provides a process for the purification of a protein of interest from a mixture comprising the steps of
 g) in an operational chromatography cycle loading a first volume of a mixture containing the protein of interest from a first container to a chromatography matrix operated such that the protein binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached;
 h) collecting flow-through containing unbound protein of interest in a second container, and
 i) re-loading the flow-through from the second container and loading a second volume of the protein of interest from the first container to the same chromatography matrix in a further operational chromatography cycle operated such that the protein of interest binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached.

The re-loading of the flow-through from the second container to the same chromatography matrix can be performed in the process of the invention after, together with or preferably prior to the loading of the second volume of the protein of interest from the first container.

In a second aspect the invention provides a process for the purification of a protein of interest from a mixture comprising the steps of
 a) in an operational chromatography cycle loading a first volume of a mixture containing the protein of interest from a first container to a chromatography matrix operated such that the dynamic binding capacity of the chromatography matrix is exceeded;
 b) collecting flow-through containing unbound protein of interest in a second container, and
 c) in a further operational chromatography cycle re-loading the flow-through from the second container and loading a second volume of the protein of interest from the first container to the same chromatography matrix, operated such that the dynamic binding capacity of the chromatography matrix is exceeded.

In a further embodiment the invention provides process according to the second aspect, wherein in step (a) the loading of the protein of interest is stopped when at least 40% 50%, 60%, 70%, 80%, 90% or 100% of the maximum static binding capacity is reached.

In a second embodiment the invention provides a process according to the first or second embodiment of the aspects of the invention, wherein the further operational chromatography cycle is the chromatography cycle immediately following.

In a third embodiment the invention provides a process according to the first and second embodiment of the aspects of the invention, wherein the concentration of protein of interest in the flow-through is measured on-line, at-line or offline. Concentration of protein of interest in the flow-through can be measured in the process according to the invention on-line, e.g. with a detector connected to the outlet of the chromatography matrix measuring in real time, at-line e.g. with samples taken from the outlet of the chromatography matrix and measured with a detector placed in proximity to the matrix, or offline e.g. with samples taken from the outlet of the chromatography matrix and measured after a delay on a detector placed distant, e.g. in a separate room from the matrix.

The concentration of protein or any other molecule of interest in the flow-through can be measured in the process according to any embodiments of the invention by any technique known in the art such as but not limited to measuring the optical absorbance or fluorescence.

The protein of interest can be determined in the flow-through in the process according to any embodiments of the invention by observing increases or decreases in the time course of the ultraviolet absorbance or fluorescence signal beyond the steady-state level of background ultraviolet absorbance or fluorescence signal caused by other protein impurities in the flow-through.

The concentration of protein of interest in the flow-through can be measured in the process according to any embodiments of the invention by ultraviolet absorbance or fluorescence at any suitable wavelength as known in the art, e.g. at 280 nm, and preferably using at a sub-optimal excitation and/or emission wavelength, such as 290 nm, 300 nm or 310 nm, to allow for detection of the protein of interest in the flow-through from the chromatography matrix even when there is signal in excess from protein impurities in the flow-through.

In a fourth embodiment the invention provides a process according to the first, second and third embodiment of the aspects of the invention, wherein the collection of the flow-through is started at a predetermined first concentration of protein of interest in the flow-through and stopped at a predetermined second concentration of protein of interest in the flow-through. In further embodiments the collection of protein of interest in the flow-through is started, for example at a concentration of 0.05 mg/ml, 0.1 mg/ml or 0.2 mg/ml of protein of interest in the flow-through and stopped, for example at a concentration of 0.6 mg/ml, 1 mg/ml, 2 mg/ml, 3 mg/ml, 4 mg/ml or 5 mg/ml of protein of interest in the flow-through.

In a fifth embodiment the invention provides a process according to the first, second, third and fourth embodiment of the aspects of the invention, wherein a predetermined fraction of the flow-through, such as for example 50%, 40%, 30%, 20%, 10% or 5% of the flow-through, is collected in the second container.

In a sixth embodiment the invention provides a process according to the first, second, third, fourth and fifth, embodiment of the aspects of the invention, wherein the flow-through collected in the second container is not processed prior to or while being re-loaded onto the chromatography matrix in a further operational chromatography cycle.

In a seventh embodiment the invention provides a process according to the first, second, third, fourth fifth and sixth embodiment of the aspects of the invention, wherein the flow-through collected in the second container is, following the completion of the chromatography cycle, directly re-loaded onto the chromatography matrix in the next operational chromatography cycle.

In an eighth embodiment the invention provides a process according to the first, second, third, fourth, fifth, sixth and seventh embodiment of the aspects of the invention, wherein the flow-through collected in the second container is processed prior to or while being re-loaded onto the chromatography matrix in a further operational chromatography cycle. Processing may be, for example stirring or agitation, dilution (e.g. in water or buffer), concentration adjustment, (e.g. using a vacuum filter assembly), pH adjustment, conductivity adjustment, buffer or solvent exchange, cooling or heating or any combination thereof.

In a ninth embodiment the invention provides a process according to the first, second, third, fourth, fifth, sixth, seventh and eighth embodiment of the aspects of the invention, wherein the flow-through from multiple separate operational chromatography cycles collected in the second container is pooled and re-loaded onto the same chromatography matrix in another cycle. The flow-through from two, three, four, five, six, seven, eight, nine, ten or more than ten operational chromatography cycle may be collected in a single second container or in a second, third, fourth or further containers and reloaded onto the chromatography matrix in a further operational chromatography cycle.

In an tenth embodiment the invention provides a process according to the first, second, third, fourth, fifth, sixth, seventh, eighth and ninth embodiment of the aspects of the invention, wherein the process comprises more than one chromatography step, and two, three, four or all chromatography steps are operated such that the flow-through containing unbound protein of interest is collected in a container other than the container from which the chromatography matrix has been loaded, and the flow-through is re-loaded from such container to the same chromatography matrix in a later operational chromatography cycle.

In a eleventh embodiment the invention provides a process according to the first, second, third, fourth, fifth, sixth, seventh, eighth, ninth and tenth embodiment of the aspects of the invention, wherein the process comprises one, two, three, four or more than four chromatography steps. Preferably, one, two, three, four or all chromatography steps are performed on a chromatography column.

In a twelfth embodiment the invention provides a process according to the eleventh embodiment of the aspects of the invention, wherein the three chromatography steps are Protein A chromatography followed by cation exchange chromatography followed by anion exchange chromatography. In one embodiment of the process of the invention the eluate of the Protein A chromatography is subjected to cation exchange chromatography operated in in bind and elute mode from where an eluate containing the protein of interest is recovered, and such eluate is subjected to anion exchange chromatography to produce a flow-through containing the protein of interest. It is understood by the skilled artisan that the process according to the invention may comprise other steps between each of the three chromatography steps, such as for example diafiltration.

In an thirteenth embodiment the invention provides a process according to the first, second, third, fourth, fifth, sixth, seventh, eighth, ninth tenth, eleventh and twelfth embodiment of the aspects of the invention, wherein the chromatography is selected from affinity chromatography, such as Protein A chromatography, anion or cation exchange chromatography, hydrophobic interaction chromatography, mixed-mode chromatography, such as hydroxyapatite chromatography, chiral chromatography or dielectric chromatography.

In a fourteenth embodiment the invention provides a process according to the first, second, third, fourth, fifth, sixth, seventh, eighth, ninth, tenth, eleventh, twelfth and thirteenth embodiment of the aspects of the invention, wherein the chromatography matrix/matrices for one, two, three, four or all chromatography steps is/are a chromatography column(s).

In a fifteenth embodiment the invention provides a process according to the first, second, third, fourth, fifth, sixth, seventh, eighth, ninth, tenth, eleventh, twelfth thirteenth and fourteenth embodiment of the aspects of the invention, wherein the protein of interest is an antibody or an antibody fragment.

In a sixteenth embodiment the invention provides a process according to the first, second, third, fourth, fifth, sixth, seventh, eighth, ninth, tenth, eleventh twelfth, thirteenth, fourteenth and fifteenth embodiment of the aspects of the invention, wherein the mixture comprises the protein of interest and prokaryotic, e.g. bacterial, host cell contaminants, such host cell protein, nucleic acid or lipid.

In a seventeenth embodiment the invention provides a process according to the first, second, third, fourth, fifth, sixth, seventh, eighth, ninth, tenth, eleventh twelfth, thirteenth, fourteenth, fifteenth and sixteenth embodiment of the aspects of the invention, wherein the mixture comprises the protein of interest and eukaryotic, e.g. mammalian, host cell contaminants, such host cell protein, nucleic acid or lipid.

In an eighteenth embodiment the invention provides a method of manufacture of a protein of interest comprising the process for purification according to the first, second, third, fourth, fifth, sixth, seventh, eighth, ninth, tenth, eleventh, twelfth and thirteenth, fourteenth, fifteenth, sixteenth and seventeenth embodiment of the aspects of the invention.

In a nineteenth embodiment of the aspects the invention provides a protein, such as an antibody or an antibody fragment, obtained by the method of the sixteenth embodiment.

In further embodiments of the aspects of the invention at least one of the chromatography columns in the process according to any of the embodiments has a bed volume of more than 1 L, more than 20 L, more than 30 L, more than 50 L, more than 75 L, more than 100 L or more than 200 L, preferably between 20 L and 200 L, 30 L and 100 L or 50 L and 100 L.

In further embodiments of the aspects the invention provides a process according to any of the embodiments, wherein one, two, three, four or all chromatography steps is/are operated on a membrane or monolith adsorber.

In further embodiments of the aspects the invention provides a process according to any of the embodiments, wherein one, two, three, four or all chromatography steps is/are is/are operated on a single chromatography column, membrane adsorber or monolith adsorber.

In a further embodiment of the aspects the invention provides a process according to any of the embodiments, wherein the collected flow-through is re-loaded from the second container onto the chromatography matrix in a subsequent operational chromatography cycle before a new batch of the mixture from the first container containing the protein interest is loaded onto said chromatography matrix. Re-loading the flow-through in a subsequent chromatography cycle before the mixture from the first container containing the protein interest allows complete binding of the recycled protein of interest by the empty column which ensures it is captured in only two cycles.

In a further embodiment of the aspects the invention provides a process according to any of the embodiments, wherein the collected flow-through is re-loaded from the second container onto the chromatography matrix in a subsequent operational chromatography cycle after or together with a new batch of the mixture from the first container containing the protein interest is loaded onto said chromatography matrix.

In further embodiments of the aspects the invention provides a process according to any of the embodiments, wherein flow-through collected in the second container is stored for at least 30 minutes, 1 hour, 2 hours, 5 hours, 10 hours, 24 hours, one day, two days, 7 days, 14 days, one month, 2 months, 6 month or a year.

The term "anion exchange chromatography" as used herein refers to a chromatography wherein the solid phase is positively charged, e.g. having one or more positively charged ligands, such as quaternary amino groups, attached thereto. Commercially available anion exchange matrices include DEAE cellulose, QAE SEPHADEX™, FAST Q SEPHAROSE™ Capto Q and Capto Q Impres (GE Healthcare), Unosphere and Nuvia Q (BioRad), GigaCap Q (Tosoh), Mustang Q XT (Pall), Fractogel Q and Eshmuno Q (Merck Millipore) and anion exchange membrane adsorbers such as SartoBind Q (Sartorius), and monolith adsorbers such as QA monoliths (Bia Separations).

The term "antibody" or "antibodies" as used herein, refers to monoclonal or polyclonal tetrameric full length antibodies comprising two heavy and two lights chains. The two heavy chains and the two light chains may be identical or different, e.g. in bispecific antibodies such as Biclonics® or the DuoBody®. The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine. Preferred molecular targets for antibodies encompassed by the present invention include CD polypeptides such as CD3, CD4, CD8, CD19, CD20, CD22, CD34, CD38, CD40 and CD40-L; FcRN; OX40; members of the HER receptor family such as the EGF receptor, HER2, HER3 or HER4 receptor; cell adhesion molecules such as LFA-1, Mac1, p150, 95, VLA-4, ICAM-1, VCAM and av/b3 integrin including either α or β subunits thereof (e.g. anti-CD11 a, anti-CD18 or anti-CD11 b antibodies); chemokines and cytokines or their receptors such as IL-1 α and β, IL-2, IL-6, the IL-6 receptor, IL-12, IL-13, IL-17A and/or IL-17F, IL-18, IL-21, IL-23, TNFα and TNFβ; growth factors such as VEGF; IgE; blood group antigens; flk2/flt3 receptor; obesity (OB) receptor; mpl receptor; CTLA-4; polypeptide C; PD1, PD-L1, PCSK9; sclerostin; etc.

The term "antibody fragment" or "antibody fragments" as used herein, refers a portion of an antibody, generally the antigen binding or variable region thereof. Examples of antibody fragments include any antibody that lacks the or has no Fc portion. Examples of antibody fragments include also such as Fab, Fab', F(ab')$_2$, and Fv and scFv fragments; as well as diabodies, including formats such as BiTEs® (Bi-specific T-cell Engagers) and DARTs™ (Dual Affinity Re-Targeting technology), triabodies, tetrabodies, minibodies, domain antibodies (dAbs), such as sdAbs, VHH and VNAR fragments, single-chain antibodies, bispecific, trispecific, tetraspecific or multispecific antibodies formed from antibody fragments or antibodies, including but not limited to Fab-Fv, Fab-scFv, Fab(Fv)$_2$ or Fab-(scFv)$_2$ constructs. Antibody fragments and derivatives as defined above are known in the art (Kontermann 2012). For the purpose of clarity Fab-Fv should be understood to refer to a construct containing one Fv region and one Fab region joined in any order, i.e. Fab-Fv, or Fv-Fab, wherein the last amino acids in one region are followed by the first amino acids in the next region or vice versa. Similarly Fab-scFv should be understood to refer to a construct containing one scFv region and one Fab region joined in any order and in the case of the Fab to either polypeptide chain, i.e. Fab-scFv, or scFv-Fab, wherein the last amino acid in one region is followed by the first amino acid in the next region or vice versa. In the same manner Fab-(Fv)$_2$ should be understood to refer to a construct containing two Fv regions and one Fab region joined in any order, i.e. Fab-Fv-Fv, Fv-Fab-Fv, or Fv-Fv-Fab, wherein the last amino acids in one region are followed by the first amino acids in the next region or vice versa. Similarly Fab-(scFv)$_2$ should be understood to refer to a construct containing two scFv regions and one Fab region joined in any order and in the case of the Fab to either polypeptide chain, resulting in 20 possible permutations. Typically these constructs include a peptide linker between the first region (e.g. Fab) and the second region (e.g. Fv). Such linkers are well known in the art, and can be one or more amino acids, typically optimized in length and composition by a skilled artisan. Alternatively said regions may be linked directly, i.e. without a peptide linker. Examples of suitable linker regions for linking a variable domain to a Fab or Fab' are described in WO 2013/068571 incorporated herein by reference, and include, but are not limited to, flexible linker sequences and rigid linker sequences. Antibody fragments can be aglycosylated or glycosylated. The term "antibody fragment" or "antibody fragments" also refers to antibody derivatives that comprise at least one antigen binding or fc receptor binding antibody domain which is covalently linked to another antibody domain, a different protein or a non-protein molecule.

The term "cation exchange chromatography" as used herein refers to a chromatography wherein the solid phase which is negatively charged, e.g. having one or more negatively charged ligands, such as for example a carboxylate or sulphonate group. Commercially available cation exchange matrices include carboxy-methyl-cellulose, sulphopropyl (SP) immobilized on agarose and sulphonyl immobilized on agarose such as Capto S, Capto Adhere and Capto S Impres (GE Healthcare), Unosphere S and Nuvia S (BioRad), GigaCap S (Tosoh), Fractogel S and Eshmuno S (Merck Millipore) or cation exchange membrane adsorbers such as SartoBind S (Sartorius) and monolith adsorbers such as SO$_3$ monoliths (Bia Separations).

The term "chromatography column" or "column" in connection with chromatography as used herein, refers to a container, frequently in the form of a cylinder or a hollow pillar which is filled with the chromatography matrix. The chromatography matrix is the material which provides the physical and/or chemical properties that are employed for purification.

The term "chromatography cycle" or "operational chromatography cycle" as used herein, refers to the operation of a single cycle of the sequence of process steps on a given allotment of chromatography matrix that may include but is not limited to some to one or more in sequential combination of the following steps: an equilibration step, a reload step, a load step, an overload step, a post load washing step, a secondary washing step, an elution step, a regeneration step, a cleaning step, a storage step and any pause or hold periods. A further cycle may therefore include a repetition of the same sequence of processing steps.

The term "dynamic binding capacity" in connection with chromatography as used herein, refers to the amount of protein of interest or other target compound that can bind to a chromatography matrix under a constant flow without having a significant amount of protein of interest or other target compound in the flow through. The dynamic binding capacity of a chromatography matrix is determined by loading a sample containing a known concentration of protein of interest. The load of the protein sample on the column is monitored and will bind to the matrix to a certain break point before unbound protein will flow through the matrix. From the breakthrough curve at a loss of, for example 10% protein, the dynamic binding capacity is found and the experiment is stopped. Often the dynamic binding capacity is defined the amount of protein of interest that can bind to the matrix under a constant flow with not more than 5%, 6%, 7%, 8%, 9%, 10%, 12%, 15%, 17% or 20% of the protein of interest lost in the flow-through, preferably of the concentration of protein of interest being loaded at the same point in time.

The term "flow-through" as used herein, refers to a liquid composition which is obtained by letting a mixture pass through or over a chromatography matrix.

The term "hydrophobic interaction chromatography" as used herein refers to a chromatography wherein the solid phase which is hydrophobic, e.g. having one or more hydrophobic ligands, such as for example a phenyl or butyl group. Commercially available hydrophobic interaction matrices include Phenyl or Butyl immobilized on agarose, such as Capto Phenyl or Capto Butyl (GE Healthcare), ToyoPearl HIC (Tosoh) and Fractogel EMD Phenyl (Merck Millipore), or immobilized on a membrane adsorber such as Sart® Bind HIC (Sartorius).

The term "membrane adsorber" or "membrane chromatography" in connection with chromatography as used herein, refers to a chromatography format, wherein a semi-permeable membrane is housed in a container through which a feed stream is supplied, and whose surfaces are affixed with resin or ligands which are the materials which provide the physical and/or chemical properties that are employed for purification.

The term "monolith chromatography" or "monolith adsorbers" in connection with chromatography as used herein, refers to a chromatography format, wherein a continuous volume of a porous polymer is housed in a container through which a feed stream is supplied, and whose surfaces are affixed with resin or ligands which is are materials which provide the physical and/or chemical properties that are employed for purification.

The term "mixed-mode" chromatography as used herein refers to a chromatography wherein the solid phase may have a mixture of different charged or uncharged ligands, such as for example hydroxyapatite. Commercially available mixed more matrices include Ceramic Hydroxyapatite (Bio-Rad) or Capto Adhere (GE Healthcare) and HA Ultrogel Hydroxyapatite (Pall).

The term "mixture", as used herein, refers to an at least partially liquid composition comprising at least one protein of interest which is sought to be purified from other substances, such as host cell proteins, DNA or other host cell components, which may also be present. Mixtures can, for example, be suspensions, aqueous solutions, organic solvent systems, or aqueous/organic solvent mixtures or solutions. The mixtures are often complex mixtures or solutions comprising many biological molecules (such as proteins, antibodies, hormones, polynucleotides and viruses), small molecules (such as salts, sugars, lipids, etc.) and even particulate matter. While a typical mixture of biological origin may begin as an aqueous solution or suspension, it may also contain organic solvents used in earlier separation steps such as solvent precipitations, extractions, and the like.

The term "static binding capacity" in connection with chromatography as used herein, refers to the maximal quantity of a protein of interest or other target compound that can bind to a chromatography matrix under static conditions without having a significant amount of protein of interest or other target compound in the flow through. The static binding capacity is normally measured in batch mode in a beaker and is usually referred to as the maximum amount of protein bound to a chromatography medium at given solvent and protein concentration conditions.

The protein of interest, such as antibody or antibody fragment, that can be purified in accordance with the process of the present invention can be produced by culturing host cells transformed with one or more expression vectors encoding the recombinant antibody or antibody fragment.

Host cells according to the embodiments of the invention are for example prokaryotic, yeast (for example without limitation *Candida boidinii, Hansenula polymorpha, Pichia methanolica, Pichia pastoris, Saccharomyces cerevisiae, Schizosaccharomyces pombe, Kluyveromyces lactis* and other *Kluyveromyces* spp., *Yarrowia lipolytica*), Myxomycete (for example without limitation *Dictyostelium discoideum*), filamentous fungi (for example without limitation *Trichoderma reesei* and other *Trichoderma* spp., *Aspergillus niger* and other *Aspergillus* spp.), moss (for example without limitation *Physcomitrella patens, Atrichum undulatum*), insect or mammalian cells. Mammalian host cells are, for example without limitation of NSO, SP2.0, 3T3 cells, COS cells, human osteosarcoma cells, MRC-5 cells, baby hamster kidney (BHK) cells, VERO cells, CHO cells, rCHO-tPA cells, rCHO-Hep B Surface Antigen cells, CHO-S cells, HEK 293 cells, rHEK 293 cells, C127 cells, rC127-Hep B Surface Antigen cells, human fibroblast cells, Stroma cells, hepatocyte cells or PER.C6 cells.

The host cells are preferably eukaryotic host cells, preferably mammalian host cells, more preferably Chinese Hamster Ovary (CHO) cells, e.g. of the DG44 strain.

For eukaryotic host cells (e.g. yeasts, insect or mammalian cells), different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA, can be selected by also introducing one or more markers, which allow for selection of host cells, which contain the expression vector. The marker may also provide for phototrophy to an auxotropic host, biocide resistance, for example without limitation antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

The eukaryotic host cells are transfected with one or more expression vectors encoding the protein of interest and subsequently cultured in any medium that will support their growth and expression of the protein of interest. The medium is a chemically defined medium that is free of animal derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L or 100,000 L, preferably between 5,000 L and 20,000 L, or to 10,000 L. Alternatively, bioreactors of a smaller scale such as between 2 L and 100 L may also be used to manufacture an antibody according to the method of the invention.

A protein of interest, such as an antibody or antigen-binding fragment that is produced in a eukaryotic host cell, such as a CHO cell, in accordance with the process and methods of the present invention is typically found in the supernatant of the cell culture. In an embodiment of the invention said supernatant is the mixture purified in the process of the invention.

Therefore in a particular embodiment of the invention, the process and methods of the invention comprises a step of centrifugation of the supernatant and recovery of the liquid phase following centrifugation in order to obtain the mixture containing the protein of interest for further purification according to the process of the invention.

Alternatively said supernatant may be recovered using clarification techniques known to the skilled artisan such as for example depth filtration. Therefore in a particular embodiment for the invention, the method comprises a step of depth filtration in order to obtain the mixture containing the protein of interest for further purification according to the process of the invention.

Alternatively, host cells are prokaryotic cells, preferably gram-negative bacteria, preferably, *E. coli* cells. Prokaryotic host cells for protein expression are well known in the art. The host cells are recombinant cells which have been genetically engineered to produce the protein of interest such as an antibody fragment. The recombinant *E. coli* host cells may be derived from any suitable *E. coli* strain including from MC4100, TG1, TG2, DHB4, DH5a, DH1, BL21, K12, XL1Blue and JM109. One example is *E. coli* strain W3110 (ATCC 27,325) a commonly used host strain for recombinant protein fermentations. Antibody fragments can also be produced by culturing modified *E. coli* strains, for example metabolic mutants or protease deficient *E. coli* strains.

An antibody fragment that can be purified in accordance with the methods of the present invention is typically found in either the periplasm of the *E. coli* host cell or in the host cell culture supernatant, depending on the nature of the protein, the scale of production and the *E. coli* strain used. The methods for targeting proteins to these compartments are well known in the art. Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter; expression of the recombinant protein can be induced by varying factors such as temperature or the concentration of a particular substance in the growth medium. Examples of inducible promoters include the *E. coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium.

Culturing of the *E. coli* host cells can take place in any suitable container such as a shake flask or a fermenter depending on the scale of production required. Various large scale fermenters are available with a capacity of more than 1,000 L up to 100,000 L. Preferably, fermenters of between 1,000 L and 50,000 L are used, more preferably of between 1,000 L and 10,000 L or 12,000 L. Smaller scale fermenters may also be used with a capacity of between 0.5 L and 1,000 L.

Fermentation of host cells such as, CHO or *E. coli*, may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete.

In one embodiment the process according to the present invention comprises prior to the loading onto the first chromatography matrix a capture step a step of centrifugation of cell culture harvest, followed by suspension of the host cells by addition of the extraction buffer.

For *E. coli* fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art.

In a particular embodiment of the method of the invention the mixture in the process of the invention according to any embodiment is generated by elution of antibody or antibody fragment bound to Protein A, for example with an elution buffer with a pH suitable to disrupt antibody or antibody fragment binding. Said pH is dependent on the specific molecule and generally determined empirically by the skilled artisan and adjusted to achieve the desired endpoint.

There are many chromatography materials available to the skilled artisan containing said native recombinant Protein A, such as for example MabSelect® (GE Healthcare), Absolute® (Novasep), Captiv A® (Repligen), or Amsphere® (JSR).

Buffers suitable for use as wash and elution buffers in Protein A chromatography are readily available in the art, and may be chosen by way of non-limiting examples from among phosphate buffered saline (PBS), Tris, histidine, acetate, citrate buffers, or MES (2-(N-morpholino)ethanesulphonic acid Imidazole), BES (N,N-(bis-2-hydroxyethyl)-2-aminoethanesulphonic acid), MOPS (3-(N-morpholino)-propanesulphonic acid), or HEPES (N-2-hydroxyethylpiperazine-N'-2-ethanesulphonic acid) buffers.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth follows in the scope of the appended claims.

As used herein, "a" or "an" may mean one or more. The use of the term "or" herein is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, "between X and Y" may mean a range including X and Y.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

EXAMPLES

Example 1

Figure 5:
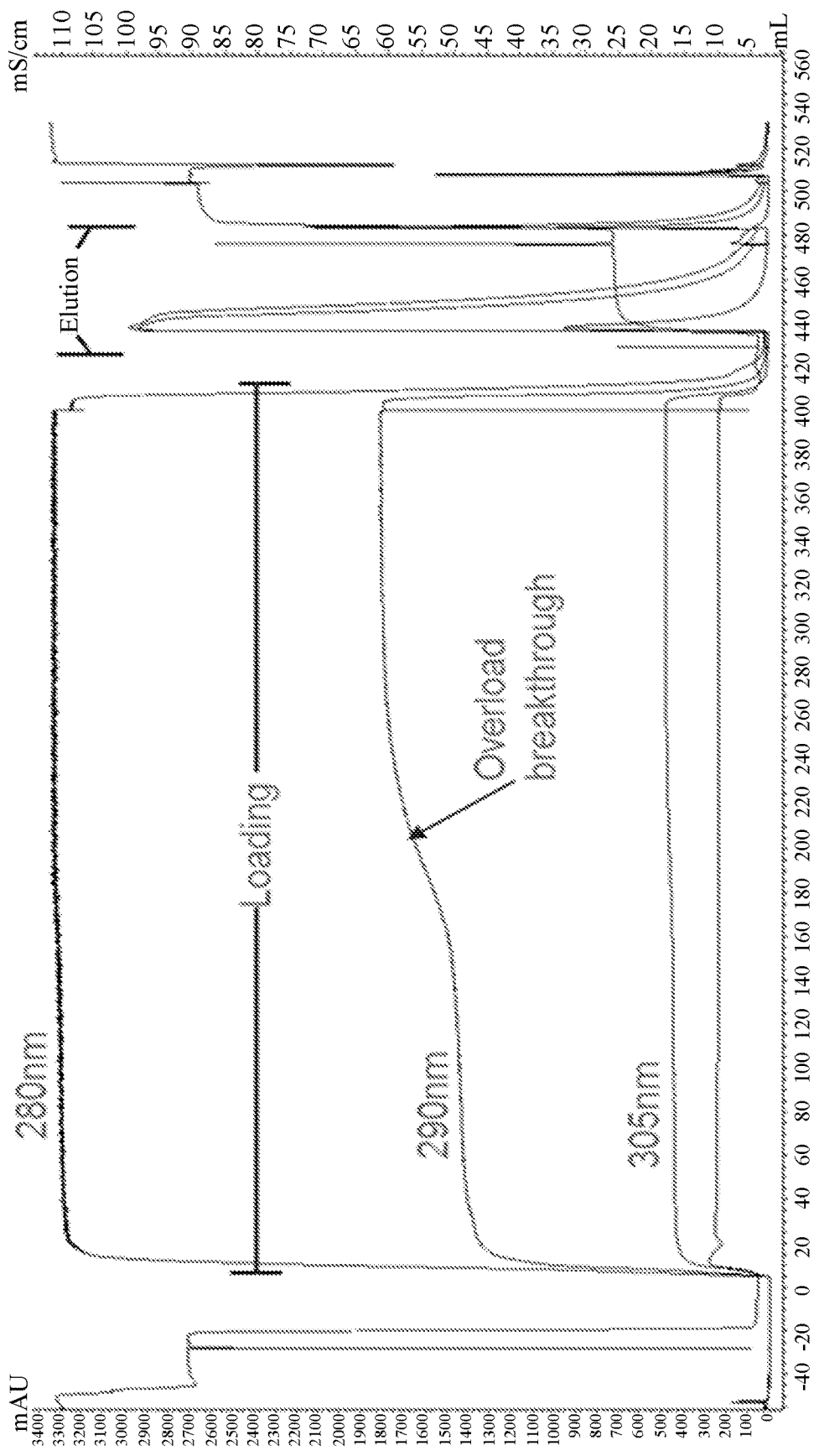
FIG. 5 shows a chromatography graph (chromatogram) of the measurements from the flow-through stream emerging from a chromatography column, with applied volume on the x-axis, measured UV-intensity on the left axis and conductivity on the right axis. In this example a column packed to a 20 cm bed height with Capto S matrix (GE Healthcare) is overloaded at 900 cm/h.

A column overload experiment was performed to establish overload performance parameters for subsequent discontinuous operation. 2×GE HiScreen CaptoS 4.67 ml 10 cm pre-packed ion exchange columns (GE Healthcare Life Sciences Product code: 28-9269-79) were attached end to end to give a 9.313 ml 20 cm bed height cation exchange column. These were attached by capillary tubing to a GE Akta Avant purification machine (product code 28930842) Buffers were attached and primed to the inlet lines. The columns were pre stripped and cleaned of any bound material using two column volumes (CVs) of a high conductivity buffer composed of 50 mM sodium acetate, 1 M sodium chloride at pH 4.5 and a conductivity of 85 mS/cm followed by a caustic buffer composed of two CVs of 0.5 M sodium hydroxide pumped through at 900 cm/h in a down-flow direction and incubated with no flow at 20° C. for 15 minutes before being washed out to equilibrate the column's matrix using 3 CVs of 50 mM sodium acetate buffer at pH 4.5 and a conductivity of 4.0 mS/cm in down-flow. An in-line conductivity monitor and three absorbance detectors were attached and calibrated to observe the flow-through. The absorbance detectors were set to 280 nm, 290 nm and 305 nm, each with a path length of 2 mm. E. coli cell extract containing an overexpressed fragment-antibody (Fab) of interest alongside host-cell impurities was prepared, and was diluted with water such that the titre of the Fab was 1.66 mg/ml with a conductivity of 10 mS/cm and a pH of 4.5. This was loaded onto the column at 900 cm/h for a total of 400 ml in down-flow for a total application of 71.3 mg per ml of chromatography matrix, fully saturating and exceeding the static or maximal binding capacity of the matrix's charged ligands for the Fab of interest at that concentration. Following this a further three CVs of 50 mM sodium acetate buffer at pH 4.5 and a conductivity of 4.0 mS/cm was applied to the column to wash off weakly bound components. FiveCVs of buffer with 50 mM sodium acetate and 225 mM sodium chloride at pH 4.5 and a conductivity of 15 mS/cm was applied to displace the strongly bound target components which were collected in a container as they emerged from the column—this collected material constituted the purified eluate. A repetition of the stripping and cleaning steps was then applied sequentially in preparation for further use (FIG. 5).

Figure 6:
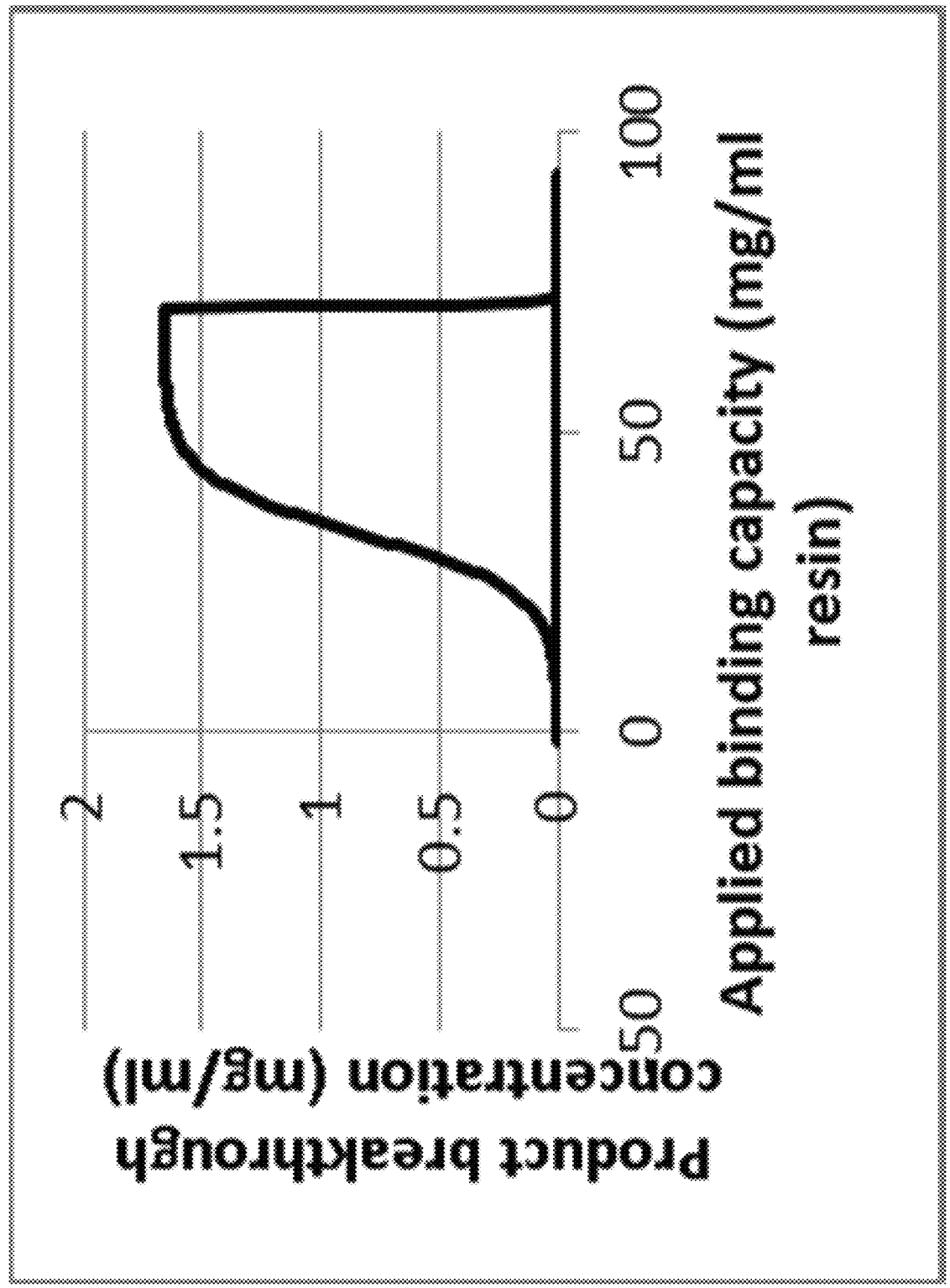
FIG. 6 shows a mathematically model of a real breakthrough experiment of a Fab target product loaded at 1.66 mg/ml titre onto a 20 cm bed height Capto S column at 900 cm/h until full saturation, with the model optimised to normalised breakthrough absorbance data at 290 nm with the baseline subtracted.

The UV detectors were used to monitor and record the relative quantity of impurity and product emerging from the column during the loading phase and the recorded quantity of applied load versus the emerging signal level as measured by absorbance of the effluent at 290 nm was input for the fitting of a computational model to the data to calculate the capacity mid-point of the breakthrough of the product and the related kinetics of the binding process (FIG. 6). This model was based on a sigmoidal fit of the breakthrough of the emerging protein of interest in the flow-through up to the loaded amount attached to an exponential decay modelling the remaining unbound protein of interest emerging in the flow-through after fresh load has stopped being applied, with additional parameters to account for the background protein impurity signal.

Figure 7:
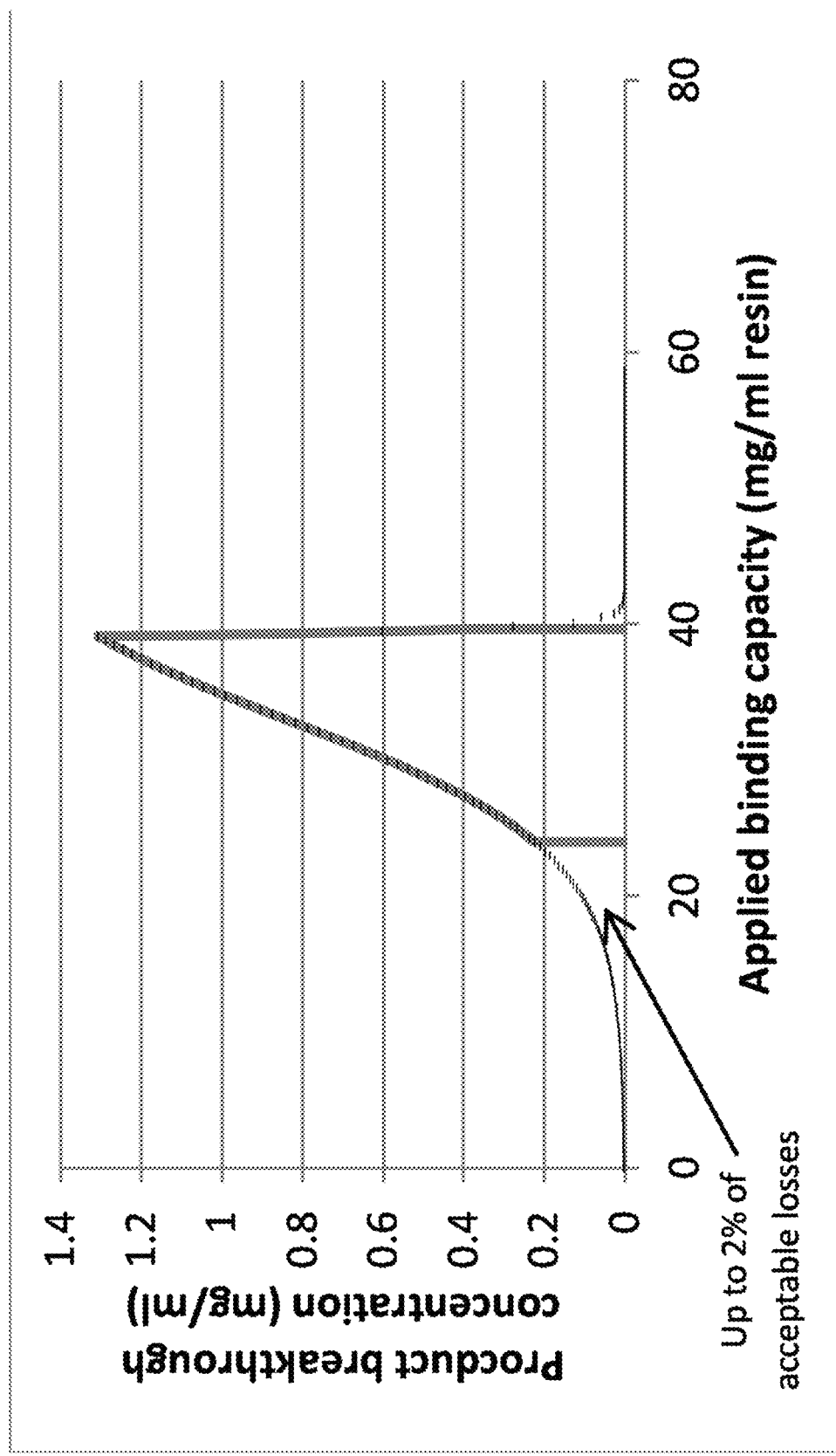
FIG. 7 shows a real example of a mathematically optimised overloading extent for the target Fab onto the Capto S column at 900 cm/h, with even computational weighting for productivity (product/time) and productive capacity (product/time/matrix quantity) in hatched black. The corresponding collection zone for recycling is shown as grey line, mathematically optimised with an allowed product loss of up to 2%.

Under the conditions described above for the CaptoS matrix operated on the feed stream with a Fab of interest with a 1.66 mg/ml titre applied at 900 cm/h. The calculated dynamic binding capacity was 20.03 mg/ml of matrix per cycle at 90% loading of the 10% breakthrough level and the productivity was calculated to be 23.52 mg/ml of matrix/hour. The static binding capacity was determined to be 32.8 mg/ml which corresponds to 161% of the dynamic binding capacity. This was used to predict the achievable capacity and productivity of the overall process over-loaded in the proposed semi-continuous methodology with a portion of the emerging overload collected in a separate container and reloaded onto the chromatography matrix in a subsequent cycle of the process. This model was iterated computationally by changing the extent of overload and the starting and ending points for the collected overload to target a desired balance of optimised capacity and productivity, with a user defined allowable-product-loss-limit set at maximum of 2%, and was predicted to operate with a real capacity of 31.40 mg/ml of matrix per cycle and with a productivity of 25.65 mg/ml of matrix/hour, representing a 9.1% improvement in productivity and a 56.8% improvement in per-cycle capacity (FIG. 7).

Figure 9:
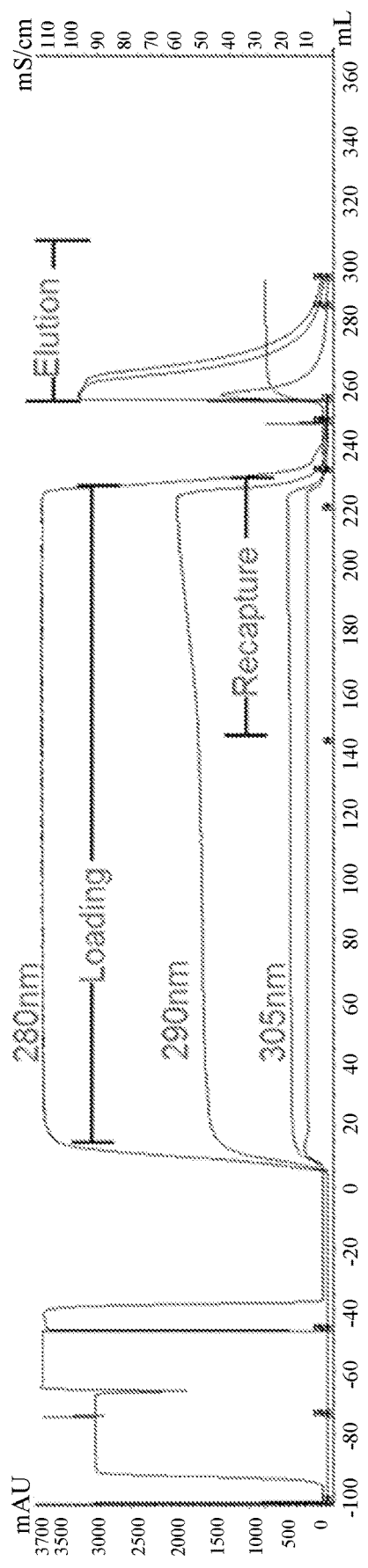
FIG. 9 shows a chromatogram of operating an initial cycle in the process according to the invention, with absorbance shown on the left axis, conductivity shown on the right axis and volume shown on the x-axis.
Figure 10:
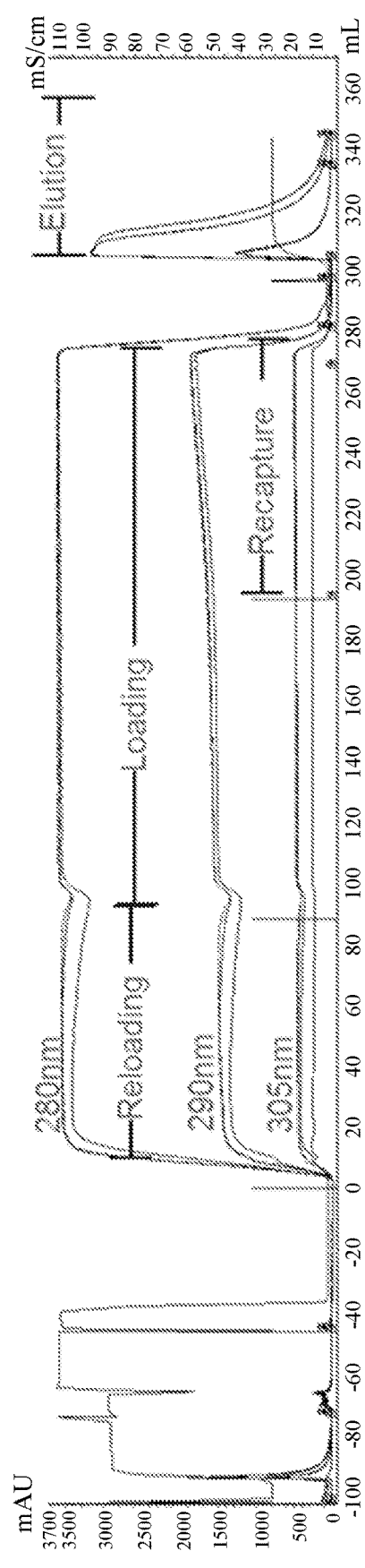
FIG. 10 shows three overlaid chromatograms of operating the $2^{nd}$ $3^{rd}$ and 4th cycles in the process according to the invention, with absorbance shown on the left axis, conductivity shown on the right axis and volume shown on the x-axis.
Figure 11:
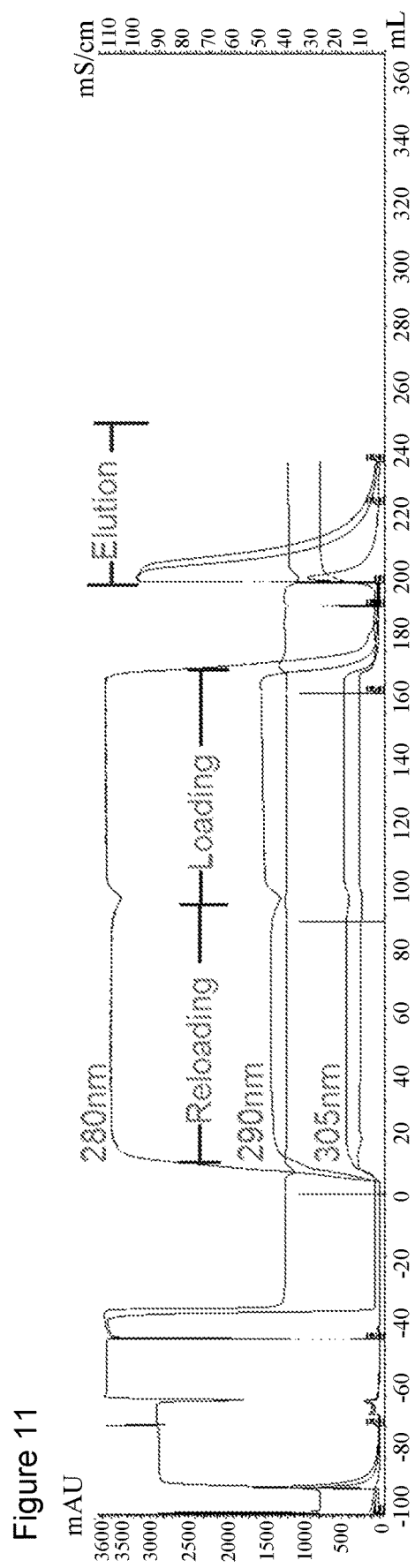
FIG. 11 shows a chromatogram of operating a fifth and final cycle in the process according to the invention, with absorbance shown on the left axis, conductivity shown on the right axis and volume shown on the x-axis.

The purification operation was repeated using these predicted settings, with the column stripped, cleaned and equilibrated in the same way. The column was then loaded with 23.56 CVs of the same batch of load projected by the computational model and controlled by continuous measurement of the loaded volume, and with overloading effluent collected after 15.44 CVs of load was applied and collected in container (the second container) for the following 9.45 CVs extending beyond the loading phase and 1.33 CVs into the subsequent wash step. Then the same wash was applied as with the previous experiment and was followed by the same elution process this time with the emerging eluate collected in a third container. This process constituted the first cycle with the overload portion collected in the second container retained for further use and the eluate portion in the third container constituting purified product which was analysed for volume, concentration and purity (FIG. 9). For the second chromatography cycle and subsequent third and fourth chromatography cycles, the regeneration, cleaning-in-place and equilibration steps were repeated at the start as before, and then the entire contents of the collected recycle (second) containers were applied totaling 9.45 CVs, followed by 19.39 CVs of an additional batch of E. coli extract. For each of these again 9.45 CVs of overload was collected back into the original second container, extending 1.33 CVs into the same subsequent wash step, and was followed by the same elution process for each cycle with the eluates again tested for performance. These chromatography cycles constituted typical running chromatography cycles in the proposed process (FIG. 10). For a fifth chromatography cycle, the stripping, cleaning, equilibration and reloading of collected overload were repeated as before, but the fresh E. coli extract was only applied to the point of traditional operational dynamic binding capacity at 90% loaded capacity as that which gives 10% breakthrough, equivalent to 7.89 CVs of additional load. The subsequent wash and elution steps were then performed in full. This constituted the final chromatography cycle with no intended overload operation and no subsequent cycling (FIG. 11). Settings can be seen in (FIG. 8). The actual capacity achieved on the matrix during a chromatography cycle in this experiment was 32.2 mg/ml which corresponds to 98.2% of the maximal static binding capacity of the matrix. For comparison the process was also operated with identical conditions in a traditional batch methodology but without the overload and recycling steps, and with the loading phase only applied to a 20.03 mg/ml capacity of the chromatography matrix which equated to 90% of the loading capacity of the 10% breakthrough level consistent with a comparable traditional operation. Results and comparison with traditional operation are shown in FIG. 12.

Example 2

Methodology:

In a parallel example of the method, 2×GE HiScreen MAb Select SuRE LX 4.67 ml 10 cm pre-packed Protein A chromatography columns (GE Healthcare Life Sciences Product code: 17-5474-05) were attached end to end to give a 9.313 ml 20 cm bed height Protein A affinity column. These were attached by capillary tubing to a GE Akta PURE purification machine (product code 29-0182-24) Similar to the prior example, buffers were attached and primed to the inlet lines. The columns were similarly pre stripped and cleaned of any bound material using two column volumes (CVs) of a citric acid buffer with a pH of 2.1 and two CVs of a 0.1 M sodium hydroxide caustic buffer pumped through at 500 cm/h in a down-flow direction and incubated with no flow at 20° C. for 15 minutes. Four CVs of equilibration buffer with a composition of 50 mM sodium phosphate at a pH 7.0 and a conductivity 6.0 mS/cm was used before applying load on all chromatography cycles, a further three CVs of the same buffer was used after applying loads to wash off weakly binding compounds and five CVs of 30 mM sodium acetate at a pH 3.7 was used to elute the bound product on all cycles. The same monitors were applied as per the previous methodology. The load contained an extracellularly expressed monoclonal antibody at a titre of 2.9 mg/ml from a mammalian host cell which was depth filtered to remove whole cells and large fragments, and the filtrate was applied to the column in down-flow up to 90 mg of target antibody/ml of the matrix, in excess of the matrix's typical static binding capacity. The measurements of the emerging flow-through was similarly used to model the breakthrough process and define optimised parameters for overloading and recycling according to the proposed methodology. These settings were then used to operate the purification process with an overloaded initial cycle, three overloaded and recycled subsequent chromatography cycles, and an under loaded final chromatography cycle. This was compared to an equivalent traditional batch methodology in identical conditions but without the overload and recycling steps, and with the loading phase only applied to a 29.68 mg/ml capacity of the chromatography matrix which equated to 90% of the loading capacity of the 10% breakthrough level consistent with a comparable traditional operation. Results and comparison with traditional operation are shown in FIG. 13.

Example 3

Methodology:

In a large scale example of the method, 190 ml of MAb Select SuRE LX 190 Protein A chromatography resin (GE Healthcare Life Sciences Product code: 17-5474-04) was packed to a height of 10 cm in an AxiChrom column (GE Healthcare Life Sciences Product code: 28901831) and attached by tubing to an AKTA pilot purification machine (GE Healthcare Life Sciences Product code 29-0086-12). Containers with buffers were attached and primed to the inlet lines as described in the previous examples. The columns were pre stripped and cleaned of any bound material using two column volumes (CVs) of a citric acid buffer with a pH of 2.1 and two CVs of a 0.1 M sodium hydroxide caustic buffer pumped through at 150 cm/h in a down-flow direction and incubated with no flow at 20° C. for 15 minutes as described in the previous examples. Five CVs of equilibration buffer with a composition of 50 mM sodium phosphate at a pH 7.0 and a conductivity 6.0 mS/cm was used before applying load on all chromatography cycles, a further three CVs of the same buffer was used after applying loads to wash off weakly binding compounds and five CVs of 60 mM sodium acetate at a pH 3.6 was used to elute the bound product on all cycles. The same monitors were applied as per the previous methodology. The load contained an extracellularly expressed monoclonal antibody at a titre of 3.9 mg/ml from a mammalian host cell which was depth filtered to remove whole cells and large fragments, and the filtrate was applied to the column at 150 cm/h. The calculated dynamic binding capacity was 47.9 mg/ml of matrix per cycle at 90% loading of the 10% breakthrough level and the productivity was calculated to be 20.9 mg/ml of matrix/hour for the traditional batch process. The static binding capacity was determined to be 77.2 mg/ml which corresponds to 143% of the dynamic binding capacity in down-flow in excess of the matrix's typical static binding capacity. The measurements of the emerging flow-through were similarly used to model the breakthrough process and define optimised parameters for overloading and recycling according to the proposed methodology. These settings were then used to operate the purification process with an overloaded initial cycle up to a load challenge of 84.1 mg/ml, three overloaded and recycled subsequent chromatography cycles up to a running capacity of 68.5 mg/ml, and an under loaded final chromatography cycle up to a capacity of 22.9 mg/ml. The actual capacity achieved on the matrix during a chromatography cycle in this experiment was 68.5 mg/ml which corresponds to 88.7% of the maximal static binding capacity of the matrix and operated with a productivity of 21.0 mg/ml of matrix/hour for the running cycles. This was compared to an equivalent traditional batch methodology in identical conditions but without the overload and recycling steps. Results and comparison with traditional operation are shown in FIG. 14.

REFERENCES

Kontermann, R. E. (2012). "Dual targeting strategies with bispecific antibodies." MAbs 4(2): 182-197.
Mahajan, E., A. George and B. Wolk (2012). "Improving affinity chromatography resin efficiency using semi-continuous chromatography." J Chromatogr A 1227: 154-162.

I claim:

1. A process for the purification of a protein of interest from a mixture comprising the steps of
   a) in an operational chromatography cycle loading a first volume of a mixture containing the protein of interest from a first container to a chromatography matrix operated such that the protein of interest binds to the chromatography matrix until 40% to 100% of the maximum static binding capacity of the chromatography matrix for the protein of interest is reached;
   b) collecting flow-through containing unbound protein of interest in a second container, and
   c) in a further operational chromatography cycle re-loading the flow-through collected in the second container to the same chromatography matrix followed by loading a second volume of the protein of interest from the first container to the same chromatography matrix, operated such that the protein of interest binds to the chromatography matrix until 40% to 100% of the maximum static binding capacity of the chromatography matrix for the protein of interest is reached.

2. The process according to claim 1, wherein the further operational chromatography cycle immediately follows the first operational chromatography cycle.

3. The process according to claim 1, wherein the collection of the flow-through is started at a predetermined first concentration of protein of interest in the flow-through and stopped at a predetermined second concentration of protein of interest in the flow-through.

4. The process according to claim 1, wherein a predetermined fraction of the flow-through is collected in the second container.

5. The process according to claim 1, wherein the flow-through is processed prior to being re-loaded onto the chromatography matrix, the processing being selected from stirring or agitation, dilution, concentration adjustment, pH adjustment, conductivity adjustment, buffer or solvent exchange, cooling or heating and any combination thereof.

6. The process according to claim 1, wherein the operational chromatography cycle is selected from affinity chromatography, ion exchange chromatography, hydrophobic interaction chromatography, mixed-mode chromatography, chiral chromatography and dielectric chromatography.

7. The process according to claim 1, wherein the process comprises three chromatography steps.

8. The process according to claim 7, wherein the process comprises Protein A chromatography followed by cation exchange chromatography followed by anion exchange chromatography.

9. The process according to claim 1, wherein the chromatography matrix is a chromatography column comprising the chromatography matrix.

10. The process according to claim 1, wherein the protein of interest is an antibody or an antibody fragment.

11. A process for the purification of a protein of interest from a mixture comprising the steps of:
    a) in an operational chromatography cycle loading a first volume of a mixture containing the protein of interest from a first container to a chromatography matrix operated such that the dynamic binding capacity of the chromatography matrix for the protein of interest is exceeded;
    b) collecting flow-through containing unbound protein of interest in a second container, and
    c) in a further operational chromatography cycle re-loading the flow-through collected in the second container to the same chromatography matrix followed by loading a second volume of the protein of interest from the first container to the same chromatography matrix, operated such that the dynamic binding capacity of the chromatography matrix for the protein of interest is exceeded.

12. The process according to claim 11, wherein in step (a) the loading of the protein of interest is stopped when at least 40% of the maximum static binding capacity is reached.

13. The process according to claim 11, wherein the further operational chromatography cycle immediately follows the first operational chromatography cycle.

14. The process according to claim 11, wherein the collection of the flow-through is started at a predetermined first concentration of protein of interest in the flow-through and stopped at a predetermined second concentration of protein of interest in the flow-through.

15. The process according to claim 11, wherein a predetermined fraction of the flow-through is collected in the second container.

16. The process according to claim 11, wherein the flow-through is processed prior to being re-loaded onto the chromatography matrix, the processing being selected from stirring or agitation, dilution, concentration adjustment, pH adjustment, conductivity adjustment, buffer or solvent exchange, cooling or heating or any combination thereof.

* * * * *

UNITED STATES PATENT AND TRADEMARK OFFICE
CERTIFICATE OF CORRECTION

PATENT NO. : 11,905,310 B2  
APPLICATION NO. : 17/327865  
DATED : February 20, 2024  
INVENTOR(S) : Michael Harry Rose Page 1 of 1

It is certified that error appears in the above-identified patent and that said Letters Patent is hereby corrected as shown below:

In the Specification

Column 14,
Line 53, "Sart® Bind" should read --SartoBind--.

Column 17,
Line 4, "DH5a" should read --DH5α--.

Signed and Sealed this
Twenty-fourth Day of September, 2024

Katherine Kelly Vidal
*Director of the United States Patent and Trademark Office*